United States Patent [19]
Getman et al.

[11] Patent Number: 5,830,888
[45] Date of Patent: Nov. 3, 1998

[54] MACROCYCLIC RETROVIRAL PROTEASE INHIBITORS

[75] Inventors: Daniel P. Getman, Chesterfield, Mo.; Robert A. Chrusciel, Portage, Mich.

[73] Assignee: Monsanto Company, St. Louis, Mo.

[21] Appl. No.: 406,614

[22] Filed: Mar. 20, 1995

Related U.S. Application Data

[63] Continuation of Ser. No. 48,720, Apr. 16, 1993, abandoned.

[51] Int. Cl.$^6$ .................. A61K 31/33; C07D 487/00; C07D 273/00; C07D 285/00
[52] U.S. Cl. ................... 514/183; 540/454; 540/460
[58] Field of Search .................. 540/454, 460; 514/183

[56] References Cited

U.S. PATENT DOCUMENTS

| H725 | 1/1990 | Gordon | 548/533 |
| 4,599,198 | 7/1986 | Hoover | 260/498.2 |

FOREIGN PATENT DOCUMENTS

| 264 795 | 4/1988 | European Pat. Off. . |
| 342 541 | 11/1989 | European Pat. Off. . |
| 346847 | 12/1989 | European Pat. Off. . |
| 2184730 | 7/1987 | United Kingdom . |
| 2200115 | 7/1988 | United Kingdom . |
| 2209752 | 5/1989 | United Kingdom . |
| 92/08700 | 5/1992 | WIPO . |

OTHER PUBLICATIONS

Tet. Lett., 33:1725–1728 (1992).
Tet. Lett., 32:2453–6 (1991).
J. Med. Chem., 34:2692–2701 (1991).
12th APS, 816–7 (1991).
Tet. Lett., 32:7655–7658 (1991).
J. Med. Chem., 34:1276–1282 (1991).
12th APS, 749–51 (1991).
J. Chem. Soc. Chem. Commun., 666–7 (1990).
J. Med. Chem., 31:284–295 (1988).
Roberts et al, Science, 248, 358–361 (1990).
Erickson et al, Science, 249:527–533 (1990).
Pure Appl. Chem., 45, 13–30 (1976).
Creger, P.L., Org. Synth., VI, 517 (1988).

Primary Examiner—Mukund J. Shah
Assistant Examiner—Brenda Coleman
Attorney, Agent, or Firm—Banner & Witcoff, Ltd.

[57] ABSTRACT

The present invention relates to N-heterocyclic-containing macrocyclic hydroxyethylamine protease inhibitor compounds, compositions and methods for inhibiting retroviral proteases.

18 Claims, No Drawings

MACROCYCLIC RETROVIRAL PROTEASE INHIBITORS

This is a Continuation of application Ser. No. 08/048,720 filed 16 Apr. 1993 abandoned.

BACKGROUND OF THE INVENTION

1. Field of the Invention

The present invention relates to retroviral protease inhibitors and, more particularly relates to novel compounds, compositions and methods for inhibiting retroviral proteases. This invention, in particular, relates to N-heterocyclic moiety-containing hydroxyethylamine protease inhibitor compounds, a composition and method for inhibiting retroviral proteases such as human immunodeficiency virus infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit replication of structural proteins and, more importantly, the retroviral protease itself. In this manner, retroviral proteases van be effectively inhibited.

Several classes of mimetic compounds are known to be useful as inhibitors of the proteolytic enzyme renin. See, for example, U.S. Pat. No. 4,599,198; G.B. 2,184,730; G.B. 2,209,752; EPO 264 795; G.B. 2,200,115 and U.S. SIR H725; and U.S. Pat. No. 4,599,198 disclose urea-containing hydroxyethylamine renin inhibitors. Also related classes of compounds are N-heterocyclic-containing hydrooxyethylamine renin inhibitors disclosed in EPO 389898. However, it is known that, although renin and HIV proteases are both classified as aspartyl proteases, compounds which are effective renin inhibitors generally cannot be predicted to be effective HIV protease inhibitors.

Macrocyclic renin inhibitors are disclosed in *Tetrahedron Letters*, Vol. 33, No. 13, pp. 1725–1728, 1992; *Tetrahedron Letters*, Vol. 32, No. 22, pp. 2453–6, 1991; *J. Med. Chem.*, 1991, 34, 2692–2701; 12th APS, pp. 816–7; *Tetrahedron Letters*, Vol. 32, No. 52, pp. 7655–7658, 1991; *J. Med. Chem.*, 1991, 34, 1276–1282; 12th APS, pp. 749–751; *J. Chem. Soc.*, Chem. Commun., 1990, pp. 666–7; *J. Med. Chem.*, 1988, 31, 284–295.

Several classes of mimetic compounds have been proposed, particularly for inhibition of proteases, such as for inhibition of HIV protease. Such mimetics include hydroxyethylamine isosteres and reduced amide isosteres. See, for example, EPO 346 847; EPO 342, 541; Roberts et al, "Rational Design of Peptide-Bases Proteinase Inhibitors, "Science, 248, 358 (1990); and Erickson et al, "Design Activity, and 2.8 Angstrom Crystal Structure of a $C_2$ Symmetric Inhibitor Complexed to HIV-1 Protease, "Science, 249, 527 (1990). EPO 346 847 discloses certain N-heterocyclic moiety-containing hydroxyethylamine protease inhibitor compounds, but does not suggest or disclose those of the present invention.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes, The subject compounds are characterized as macrocyclic-containing hydroxyethylamine inhibitor compounds.

DETAILED DESCRIPTION OF THE INVENTION

In accordance with the present invention, there are provided novel retroviral protease inhibiting compounds or a pharmaceutically acceptable salt, prodrug or ester thereof.

Thus, the present invention are compounds represented by the formula (I)

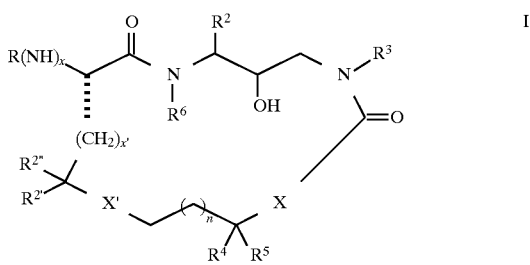

or a pharmaceutically acceptable salt, prodrug or ester thereof, and wherein:

R represents hydrogen, alkoxycarbonyl, aryloxycarbonylalkyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heteroaralkoxycarbonyl, heterocyclyalkanoyl, heterocyclylalkoxycarbonyl, heteroarylcarbonyl, heteroaryloxycarbonyl, heteroaroyl, alkyl, aryl, aralkyl, aryloxyalkyl, heteroaryloxyalkyl, hydroxyalkyl, alkylaminocarbonyl, arylaminocarbonyl, aralkylaminocarbonyl, aminalkanoyl, aminocarbonyl, amincarbonylalkyl, alkylaminoalkylcarbonyl, and mono- and disubstituted aminoalkanoyl radicals wherein the substituents are selected from the group consisting of alkyl, aryl, aralkyl, cycloalkyl, cycloalkylalkyl, heteroaryl, heteroaralkyl, heterocycloalkyl, and heterocycloalkylalkyl radicals, or in the case of disubstituted aminoalkanoyl, said substituents along with the nitrogen atom to which they are attached from a heterocyclyl or heteroaryl radical;

x and x' independently represent 0 or 1;

$R^{2'}$ and $R^{2''}$ independently represent hydrogen; $CO_2R$, $CH_2CO_2R$, $CH_2CONH_2$, $CH_2SO_2CH_3$, and $R^2$ as defined herein and wherein R is independently as defined above;

$R^2$ represents alkyl, aryl, cycloalkyl, cycloalkylalkyl, and aralkyl radicals, which radicals are optionally substituted with a substituent selected from the group consisting of —$NO_2$, —$OR^{15}$, —$SR^{15}$, and halogen radicals, wherein $R^{15}$ represents hydrogen and alkyl radicals;

$R^3$ represents alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

n represents an integer of from 1 through 5, preferably 2, 3 or 4.

$R_4$ and $R_5$ independently represent hydrogen and $R^2$;

X represents O, S, $CH_2$ and $NR^1$; wherein $R^1$ represents hydrogen and alkyl;

X' represents $CH_2$, S, S(O), $S(O)_2$ or $R^{10}NH$ wherein $R^{10}$ represents $(CH_2)_qC(O)$ wherein q is 0 or 1;

$R^6$ represents hydrogen and alkyl radicals; preferably hydrogen.

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, n-butyl, isobutyl, sec-butyl, tert-butyl, pentyl, isoamyl, hexyl, octyl and the like. The term "thioalkyl" means aralkyl radical having at least one sulfur atom, wherein alkyl has the significance given above. An example of a thioalkyl is —$C(CH_3)_2SCH^3$. The corresponding sulfoxide and sulfone of this thioalkyl are —$C(CH_3)_2S(O)CH_3$ and —$C(CH_3)_2S(O)_2CH_2$, respectively. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, ally, 1,4-butadienyl and the like. The term "alkynyl", alone or in combination, means a straight-chain hydrocarbon radical having one or more triple bonds and containing from 2 to about 10 carbon atoms. Examples of alkynl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like. The term "cycloalkylalkyl" means an alkyl radical as defined above which is substituted by a cycloalkyl radical containing from about 3 to about 8, preferably from about 3 to about 6, carbon atoms. The term "aryl", alone or in combination, means a phenyl or naphthyl radical which optionally carries one or more substituents selected from alkyl, alkoxy, halogen, hydroxy, amino, nitro and the like, such as phenyl, p-tolyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O-aralkyl in which the term "aralkyl" has the significance given above. An example of an aralkoxy-carbonyl radical is benzyloxycarbonyl. The term "aryloxy", alone or in combination, means a radical of the formula aryl-O— in which the term "aryl" has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclylalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., =N—) by oxido and which is attached via a carbon atom. The heteroaryl portion of a heteroaroyl, heteroaryloxycarbonyl, or heteroaralkoxycarbonyl group or the like is an aromatic monocyclic, bicyclic, or tricyclic heterocyle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol-4-yl, 1-benzyloxycarbonylimidazol-4-yl, etc.), pyrazolyl, pyridyl, pyrazinyl, pyrimidinyl, furyl, thienyl. triazolyl, oxazolyl, thiazolyl, indolyl (e.g., 2-indolyl, etc.), quinolinyl (e.g., 2-quinolinyl, 3-quinolinyl, 1-oxido-2-quinolinyl, etc.), isoquinolinyl (e.g., 1-isoquinolinyl, 3-isoquinolinyl, ets.), tetra hydroquinolinyl (e.g., 1,2,3,4-tetrahydro-1-oxoisoquinolinyl, etc.), quinoxalinyl, beta-carbolinyl, 2-benzofurancarbonyl, 1-,2-, 4-, or 5-benzimidazolyl, and the like. The term "cycloalkylalkoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclylalkanoyl" is an acyl radical derived from a heterocyclyl-substituted alkane carboxylic acid wherein heterocyclyl has the significance given above. The term "heterocyclyloxycarbonyl" means an acyl group derived from heterocyclyl-O—COOH wherein heterocyclyl is as defined above. The term "heterocyclylalkanoyl" means an acyl radical of the formula aryl-O-alkanoyl wherein aryl and alkanoyl have the significance given above. The term "heterocyclylalkoxycarbonyl" means an acyl radical derived from heterocyclyl-substituted alkane-O—COOH wherein heterocyclyl has the significance given above. The term "heteroaryloxycarbonyl" means an acyl radical derived from a carboxylic acid represented by heteraryl-O—COOH wherein heteroaryl has the significance given above.

The term "aminocarbonyl" alone or in combination, means an amino-substituted carbonyl(carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like. The term "aminoalkanoyl" means an acyl radical derived from an amino substituted alkanecarboxylic acid wherein the amino group can be a primary, secondary or tertiary amino group containing substituents selected from the group consisting of hydrogen cycloalkyl, cycloalkylalkyl radicals and the like, examples of which include N, N-dimethylaminoacetyl and N-benzylaminoacetyl. The term "halogen" means fluorine, chlorine, bromine or iodine. The term "leaving group" generally refers to groups readily displaceable by a nucleophile, such as an amine, a thiol or an alcohol nucleophile. Such leaving groups are will known and include carboxylates, N-hydroxysuccinimide, N-hydroxybenzotriazole, halides, triflates, tosylates, —OR and —SR and the like. Preferred leaving groups are indicated herein where appropriate. The term "N-heterocyclic moiety" is a heterocyclic radical with a nitrogen radical bond site which may be a heterocycloalkyl or heteroaryl, wherein heterocycloalkyl and heteraryl have the significance given above, with the addition that polycyclic heteroaryl may be fully aromatic or partially aromatic, for example, a fused heterocycloalkylaryl and a fused heteroarylcycloalkyl, and heterocycloalkyl and cycloalkyl may also be bridged. Preferable, the N-heterocyclic moiety has 5, 6 or 7 members when monocyclic; 5, 6, or 7 members in a ring with 1, 2 or 3 members in a bridge when a bridged monocyclic; 11, 12 or 13 members when bicyclic; and 11 to 16 members when tricyclic.

Procedures for preparing the compounds of Formula I are as set forth below in Scheme 1. It should be noted that the general procedure is shown as it relates to preparation of compounds having the specified stereochemistry, for example, wherein the stereochemistry about the hydroxyl group is designated as (R). However such procedures are generally applicable to those compounds of opposite configuration, e.g., where the stereochemistry about the hydroxyl group is (S). The terms (R) and (S) configuration are as defined by the IUPAC 1974 Recommendations for Section E, Fundamental Stereochemistry, Pure Appl. Chem. (1976)45, 13–30.

Preparation of Compounds of Formula I

An amino alcohol of the formula

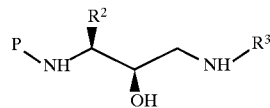

can be prepared by a method disclosed in PCT/US91/8613 incorporated herein by reference therefor.

When X is NH, the amino alcohol can be reacted with a carboxylic acid of the structure;

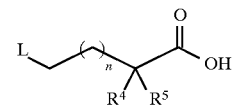

where L is a leaving group such as chloro, bromo, iodo or methanesulfonate, or the like, by a Curtius rearrangement of the carboxylic acid in the presence of diphenylphosphoryl azide and triethylamine in a solvent such as toluene at a temperature of 25° C.–150° C., which generates an isocyanate of the structure;

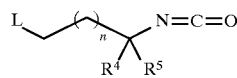

the resulting isocyanate can then be reacted with the amino alcohol to provide a compound of the formula;

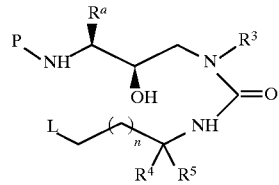

The amino protecting group P can then be selectively removed by methods known to those ordinarily skilled in the art. For example, when P is a t-butyloxycarbonyl group, it can be removed by treatment with an acid such as trifluoroacetic acid or hydrochloric acid, or the like. When P is a carbobenzyloxy group, it can be removed by hydrogenolysis in the presence of a palladium-on-carbon catalyst, preferably the hydrogenation is performed in the presence of an acid, such as p-toluenesulfonic acid, to protonate the resulting amine. The amine salt can then be neutralized and coupled to a protected amino acid having the structure;

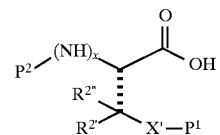

where $P^1$ is a sulfur protecting group such as acetyl, benzoyl or carbobenzyloxy, and $P^2$ is an amino protecting group such as t-butyloxycarbonyl or benzyloxycarbonyl. Preferably both $P^1$ and $P^2$ are carbobenzyloxycarbonyl. The coupling can be carried out using a variety of coupling methods well-known to those in the art. Suitable methods include mixed anhydrides or carbodiimides in the presence of N-hydroxybenzotriazole. The resulting product has the following formula;

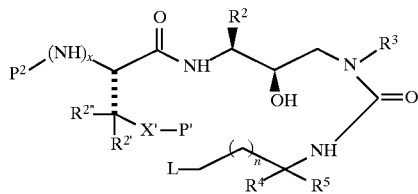

The sulfur protecting group $P^1$ can then be selectively removed using methods well-known to those in the art. For example, when $P^1$ is the carbobenzyloxycarbonyl group it can be removed by treatment with ammonia. The resulting free thiol can then displace the leaving group L to form a compound at the following structure;

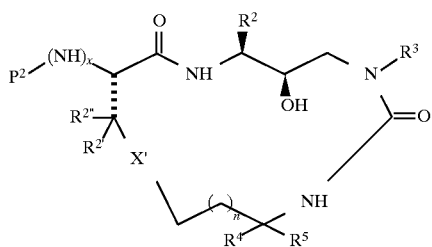

The amino protecting group $P^2$ can then be selectively removed using well-known methods. For example, when $P^2$ is a carbobenzyloxycarbonyl group it can be removed by treatment with hydrobromic acid in acetic acid. The resulting amine can then be coupled to an acid chloride or carboxylic acid to form the desired compounds of the structure;

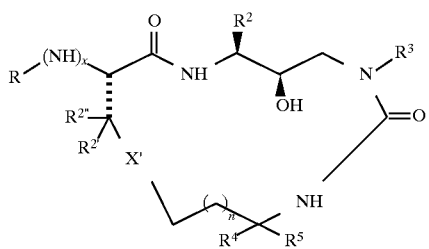

If one desires, the sulfide (X'=S), can be oxidized to either the sulfoxide (X'=SO) or sulfone (X'=SO$_2$) by well-known methods, which include; meta-chloroperbenzoic acid, hydrogen peroxide in acetic acid, sodium perborate in acetic acid, and the like.

In order to prepare compounds where X is O or NR$^1$, the amino alcohol can be reacted with a chloroformate or carbamoyl chloride of the following structure;

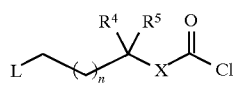

where L is as described above and X is either O or N—R?, in the presence of a base such as pyridine, triethylamine or the like, to provide a compound of the structure:

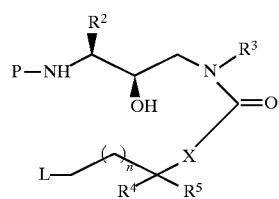

The resulting compound can then be carried through the same sequence of reactions as described above for X=NH to provide final compounds of the following structure;

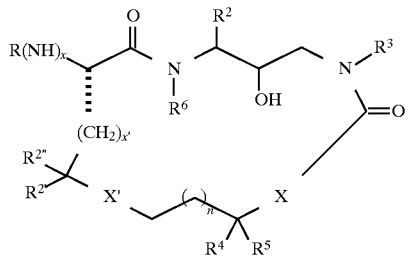

For the final compounds wherein x' is 1, the protected amino acid described above may be an appropriate amino acid producing corresponding intermediates in the above described process.

Contemplated equivalents of the respective general formulas set forth above for the antiviral compounds and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Specifically, one can prepare selected compounds of the Formula I according to the following Schemes 1, 2, 3 and 4, and the Examples 1–9.

Scheme 1
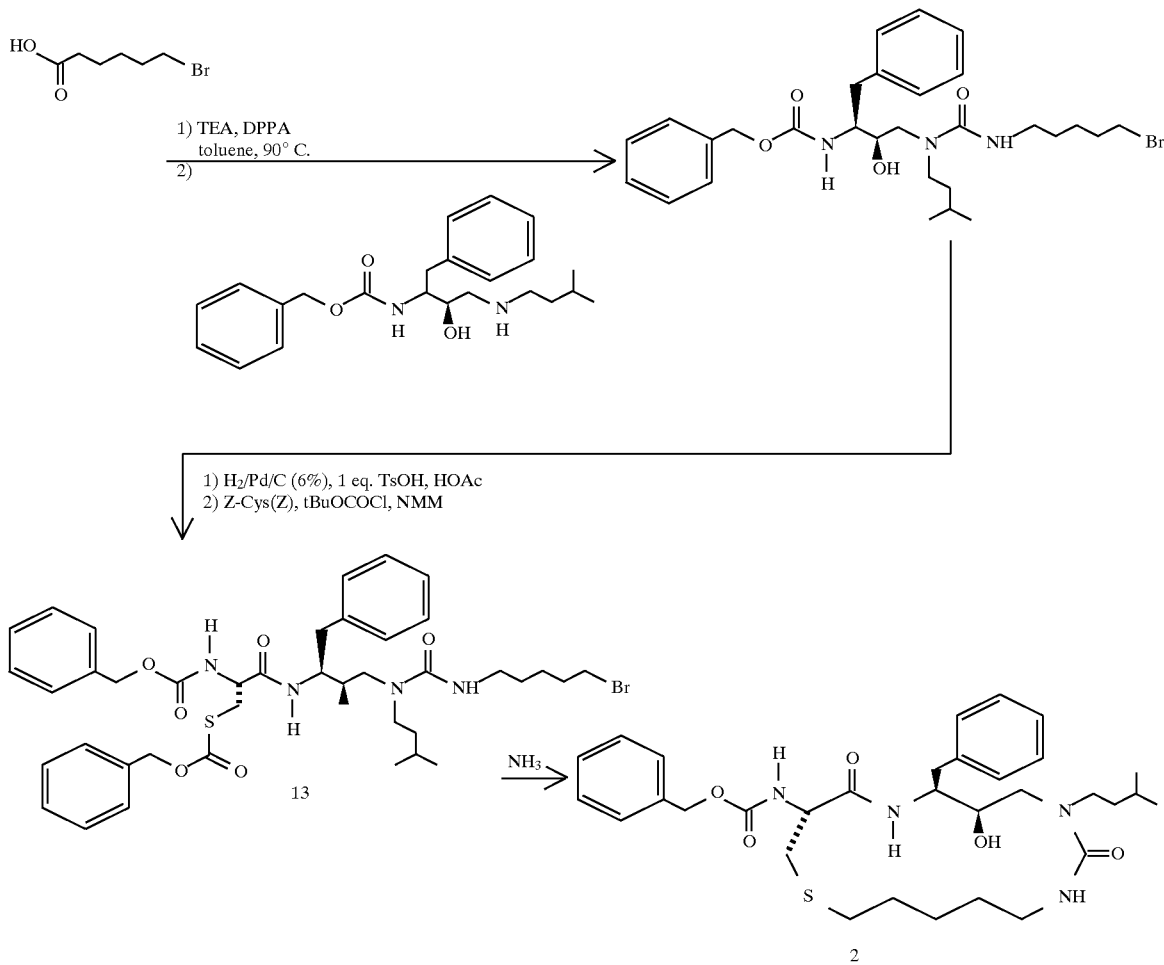
Scheme 2
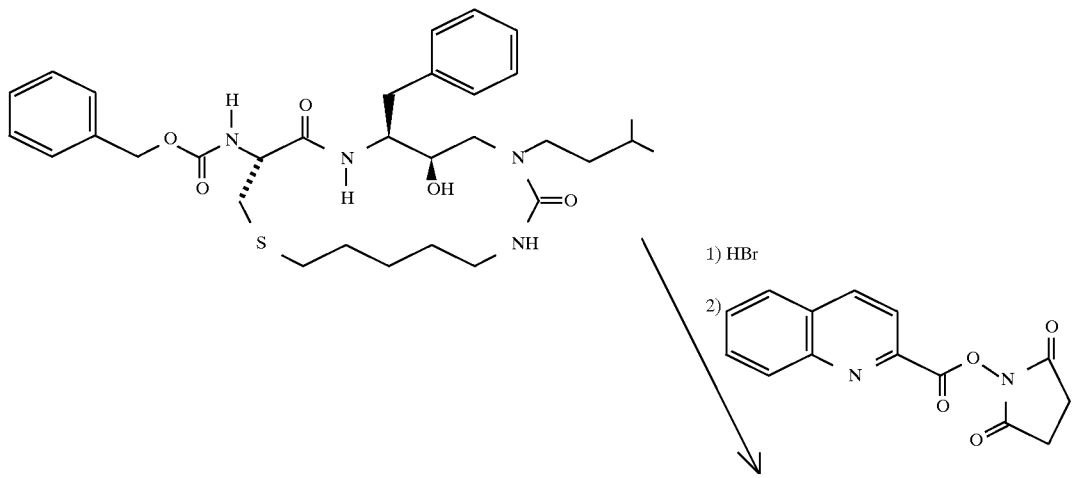

-continued
Scheme 2
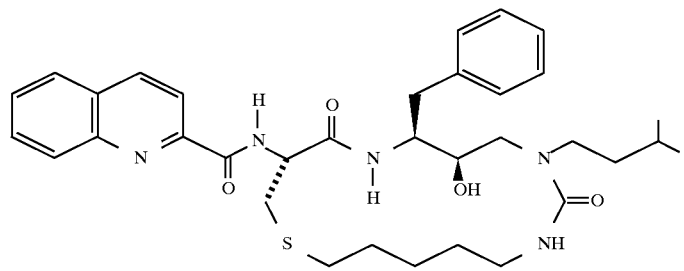
Scheme 3
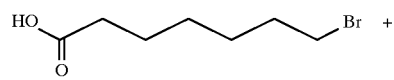
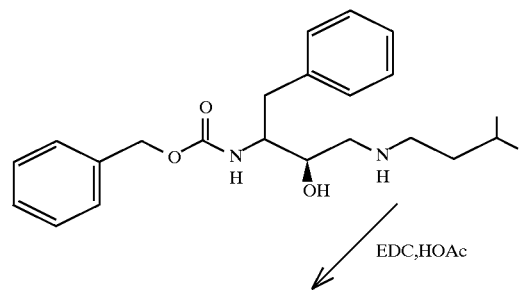
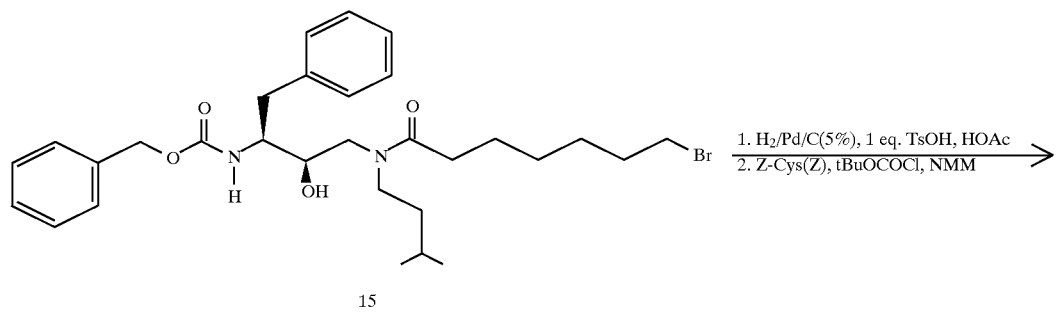
15
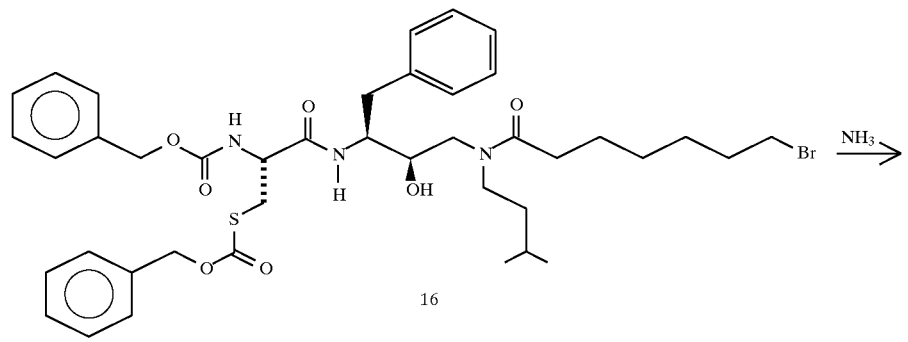
16

-continued
Scheme 3

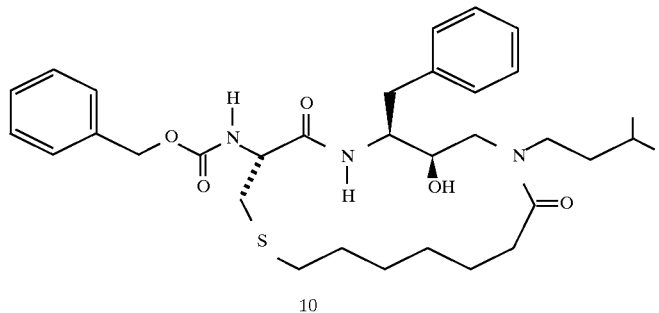

10

Alternatively, one can further prepare a selected compound using a compound of the formula 12 from above as shown in the following Scheme 4.

Scheme 4

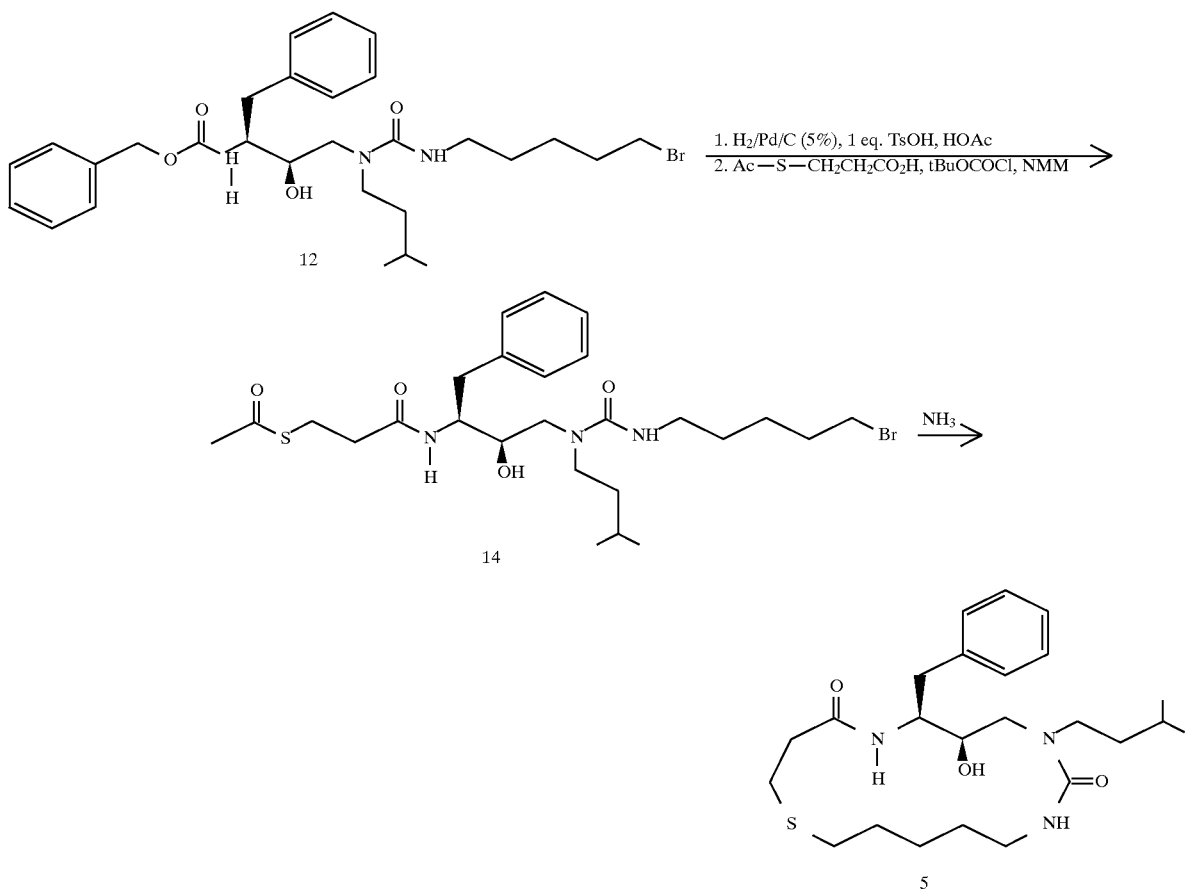

The compound 11 is prepared by methods disclosed in PCT WO 9208700A1 which is incorporated by reference therefor.

In the following examples, melting points were determined on a Fisher-Johns melting point apparatus and are uncorrected. All reagents were used as received without purification. All proton and carbon NMR spectra were obtained on either a Varian VXR-300 or VXR-400 nuclear magnetic resonance spectrometer using tetramethylsilane as internal standard. Gas chromatograph was performed on a Varian 3400 chromatography system. All instruments were utilized according to the manufacturer's directions.

EXAMPLES

Example 1

Preparation of 12

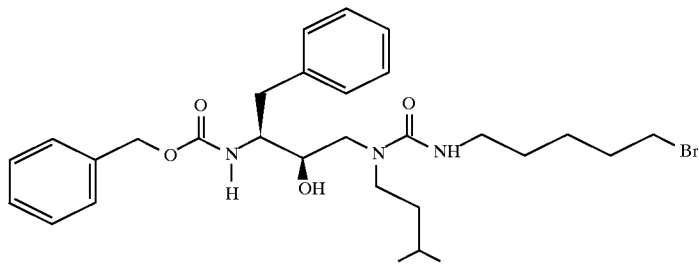

12

Triethylamine (516 mg, 5.1 mmol) was added dropwise to a solution of 6-bromohexanoic acid (1.0 g, 5.1 mmol) in toluene (40 mL) at 90° C. under an atmosphere of nitrogen. Diphenylphosphoryl azide (1.4 g, 5.1 mmol) was added and the solution stirred at 90° C. for 45 minutes. The solution was cooled to 0°–5° C. and N-3(S)-[(phenylmethylcarbamoyl)amino- 2(R)-hydroxy-4-phenylbutyl]—N—((3-methyl)butyl)amine, 11 (1.77 g, 4.6 mmol) in toluene (30 mL) was added. The solution was stirred at 0°–5° C. for 1 hour then at room temperature overnight. Volatiles were removed at reduced pressure and the residue dissolved in ethyl acetate. The organic layer was washed with 0.25N aqueous HCl, 5% aqueous NaHCO$_3$ and brine, dried (MgSO$_4$), filtered and evaporated. Purification by flash chromatography (ethyl acetate-hexanes, 1:4) provided 12 (2.14 g, 73%) as an oil, R$_f$ 0.62 [ethyl acetate-hexanes (1:1)], HRMS MH$^+$ calcd for C$_{29}$H$_{43}$N$_3$O$_4$Br 576.2437, found 576.2491.

Example 2

Preparation of 13

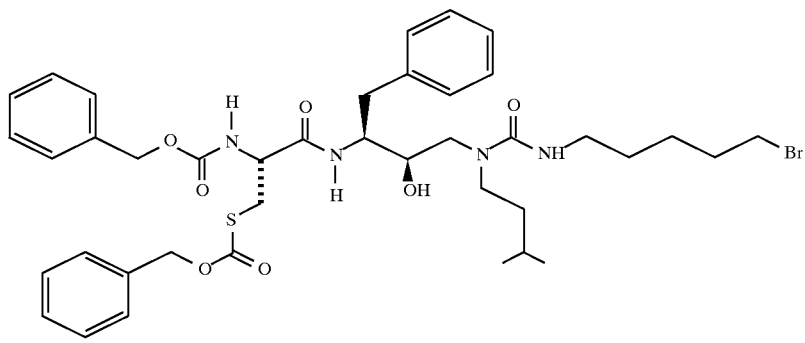

13

To a solution of 12 (152 mg, 0.26 mmol) and 4-toluenesulfonic acid (50 mg, 0.26 mmol) in acetic acid (40 mL) was added 5% palladium on carbon (30 mg, 20% w/w). The mixture was hydrogenated at approx. 4 psi H$_2$ at room temperature until complete by TLC (90 minutes).

The catalyst was filtered and the solvent evaporated to provide the crude toluenesulfonate which was used without further purification.

In a separate flask, N,S-bis-Z-cysteine (123 mg, 0.32 mmol), and N-methylmorpholine (32 mg, 0.32 mmol) were dissolved in anhydrous THF (5 mL) and cooled to 0°–5° C. under an atmosphere of nitrogen. Isobutyl chloroformate (43 mg, 0.32 mmol) was added and the mixture stirred at 0°–5° C. for 5 minutes. This mixture was added by syringe to the previously described toluenesulfonate followed by N-methylmorpholine (27 mg, 0.26 mmol) and additional anhydrous THF (5 mL). After stirring at 0°–5° C. for 1 hour then room temperature overnight, the mixture was diluted with ethyl acetate washed with 0.25N aqueous HCl, 5% aqueous NaHCO$_3$, and brine, dried (MgSO$_4$) filtered and evaporated to provide the crude product. Purification by flash chromatography [CH$_2$Cl$_2$—MeOH (1%)] afforded 13 (163 mg, 76%) as an oil, R$_f$ 0.65 [CH$_2$Cl$_2$—MeOH (5%)], HRMS [M+Li]$^+$ calcd for C$_{40}$H$_{53}$N$_4$O$_7$SBrLi 819.2978, found 819.3008.

Example 3

Preparation of 2

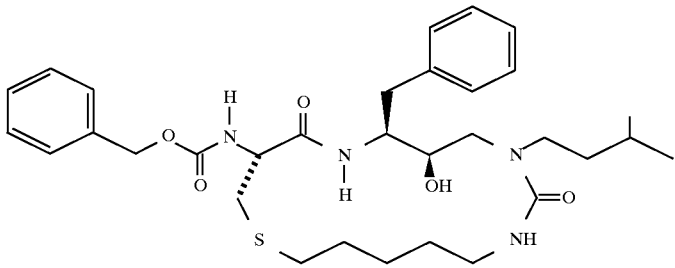

2

Anhydrous ammonia (120 mL) was condensed into a 250 mL 3-neck round bottom flask equipped with a dry ice condenser cooled with dry ice-acetone. A solution of 13 (80 mg, 0.098 mmol) in anhydrous THF (15 mL) was added dropwise to the liquid ammonia with stirring at −78° C. The cooling bath was removed and the mixture allowed to reflux for 3 h. The ammonia was removed with a stream of nitrogen overnight and the residue purified by flash chromatography [$CH_2Cl_2$—MeOH (0–3%)] to provide 2 (36 mg, 61%) as a hygroscopic amorphous solid, $R_f$ 0.50 [$CH_2Cl_2$—MeOH (5%)], HRMS [M+Li]$^+$ calcd for $C_{32}H_{46}N_4O_5SLi$ 605.3349, found 605.3341.

Example 4

Preparation of 14

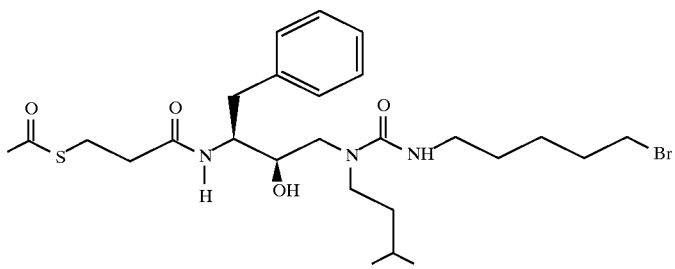

14

To a solution of 12 (226 mg, 0.39 mmol) and 4-toluenesulfonic acid (74 mg, 0.39 mmol) in acetic acid (40 mL) was added 5% palladium on carbon (45 mg, 20% w/w). The mixture was hydrogenated at approx. 4 psi $H_2$ at room temperature until complete by TLC (90 minutes).

The catalyst was filtered and the solvent evaporated to provide the crude toluenesulfonate which was used without further purification.

In a separate flask, S-acetyl-3-mercaptopropionic acid (69 mg, 0.47 mmol), and N-methylmorpholine (47 mg, 0.47 mmol) were dissolved in anhydrous THF (5 mL) and cooled to 0°–5° C. under an atmosphere of nitrogen. Isobutyl chloroformate (64 mg, 0.47 mmol) was added and the mixture stirred at 0°–5° C. for 5 minutes. This mixture was added by syringe to the previously described toluenesulfonate followed by N-methylmorpholine (39 mg, 0.39 mmol) and additional anhydrous THF (5 mL). After stirring at 0°–5° C. for 1 hour then room temperature overnight, the mixture was diluted with ethyl acetate washed with 0.25N aqueous HCl, 5% aqueous $NaHCO_3$, and brine, dried ($MgSO_4$) filtered and evaporated to provide the crude product. Purification by flash chromatography [$CH_2Cl_2$—MeOH (1%)] afforded 14 (97 mg, 43%) as an oil, $R_f$ 0.55 [$CH_2Cl_2$—MeOH (5%)], HRMS [M+Li]$^+$ calcd for $C_{26}H_{42}N_3O_4SBrLi$ 578.2240, found 578.2202.

Example 5

Preparation of 5

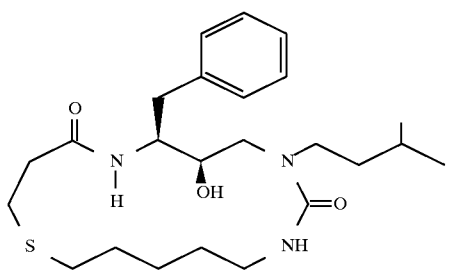

5

Macrocyclization of 14 (94 mg, 0.164 mmol) as described for the preparation of 2 afforded after purification by flash chromatography [$CH_2Cl_2$—MeOH (0–3%)] 5 (62 mg, 84%) as an amorphous solid, $R_f$ 0.52 [$CH_2Cl_2$—MeOH (5%)], HRMS [M+Li]$^+$ calcd for $C_{24}H_{39}N_3O_3SLi$ 456.2872, found 456.2896.

Example 6

Preparation of 15

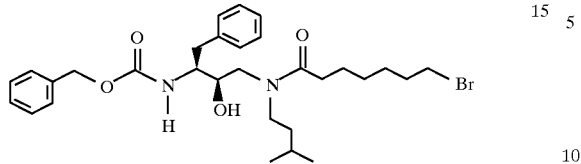

To a solution of 7-bromoheptanoic acid (500 mg, 2.39 mmol) and 11 (amino alcohol) (825 mg, 2.15 mmol), and 1-hydroxybenzotriazole (366 mg, 2.39 mmol) in $CH_2Cl_2$—DMF (1:1, 40 mL) at 0°–5° C. was added 1-(3-dimethylaminopropyl)-3-ethylcarbodiimide hydrochloride (EDC) (454 mg, 2.39 mmol). The solution was stirred at 0°–5° C. for 1 hour then room temperature overnight. After removing the volatiles in-vacuo, the residue was dissolved in ethyl acetate and washed with 0.25N aqueous HCl, 5% aqueous $NaHCO_3$, and brine, dried ($MgSO_4$) and evaporated. Purification by flash chromatography [hexanes and a gradient of ethyl acetate (25–75%)] afforded 15 (950 mg, 69%) as an oil, $R_f$ 0.35 (ethyl acetate-hexanes, 1:1), HRMS $MH^+$ calcd for $C_{30}H_{44}N_2O_4Br$ 575.2485, found 575.2513.

Example 7

Preparation of 16

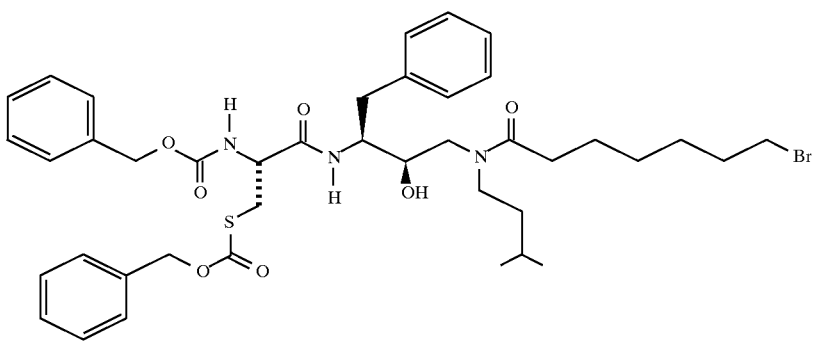

Hydrogenation of 15 (240 mg, 0.41 mmol) and mixed anhydride coupling to N,S-bis-Z-cysteine as described for the synthesis of 14 provided after purification by flash chromatography [$CH_2Cl_2$—MeOH (1%)] 16 (280 mg, 84%) as an oil, $R_f$ 0.54 [$CH_2Cl_2$—MeOH (5%)], HRMS $[M+Li]^+$ calcd for $C_{41}H_{54}N_3O_7Li$ 818.3026, found 818.2979.

Example 8

Preparation of 10

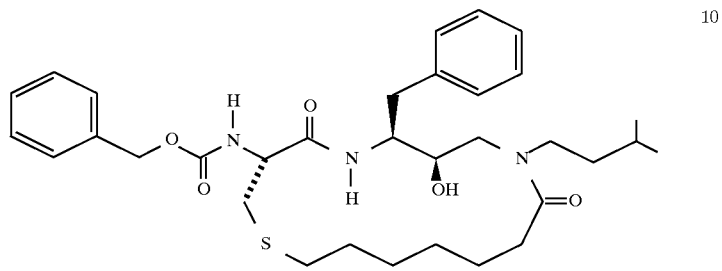

Macrocyclization of 16 (120 mg, 0.15 mmol) as described for the preparation of 2 afforded after purification by flash chromatography [$CH_2Cl_2$—MeOH (1%)] 10 (70 mg, 78%) as an amorphous solid, $R_f$ 0.45 [$CH_2Cl_2$—MeOH (5%)], HRMS $[M+Li]^+$ calcd for $C_{33}H_{47}N_3O_5SLi$ 604.3396, found 604.3412.

Example 9

Preparation of 9

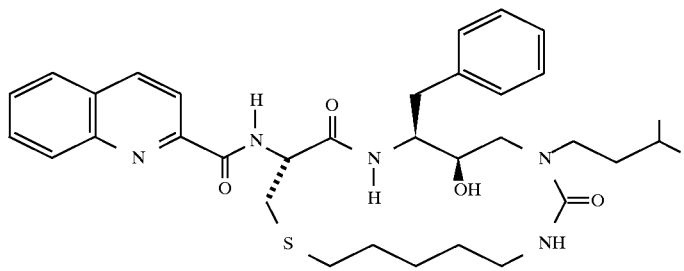

9

To a solution of 2 (32 mg, 0.05 mmol) in acetic acid (1.5 mL) was added HBr (33% in acetic acid) (1 mL) at room temperature with the exclusion of moisture. The solution was stirred for 25 minutes, diluted with ethyl ether (100 mL) and cooled to 0°–5° C. for 2 hours. The crystals were recovered by filtration, dried in a desiccator over KOH and $P_2O_5$ and used without further purification. The hydrobromide salt was dissolved in anhydrous DMF (3 mL) and cooled to 0°–5° C. under an atmosphere of nitrogen. Quinaldic hydroxysuccinamide ester (15 mg, 0.057 mmol) and triethylamine (9 mg, 0.09 mmol) were added and the solution stirred at 0°–5° C. for 1 hour then room temperature overnight. Solvents were removed in-vacuo, and the residue purified by flash chromatography [$CH_2Cl_2$—MeOH (1%)] to provide 9 (14 mg, 45%) as an amorphous solid, $R_f$ 0.60 [$CH_2Cl_2$—MeOH (5%)], HRMS MH$^+$ calcd for $C_{34}H_{45}N_5O_4S$ 620.3271, found 620.3249.

Example 10

Preparation of 6-bromo-2,3-dimethylhexanoic acid

The title compound was prepared as described (Creger, P. L. *Org. Synth.*, 1988, VI, 517) from isobutyric acid (9.67 g, 109.8 mmol), and 1,4-dibromobutane (71.1 g, 329.2 mmol). The product was purified by flash chromatography ($CHCl_3$) to provide the acid (1.4 g, 6%) as a oil, MS MH$^+$ calcd for $C_8H_{16}O_2Br$ 223.0334, found 223.0353.

Example 11

Preparation of 5-chloro-2,3-dimethylpentanoic acid

The title compound was prepared as described for 6-bromo-2,3-dimethylhexanoic acid from isobutyric acid (9.67 g, 109.8 mmol), and 1,3-dichloropropane (37.2 g, 329.2 mmol). The product was purified by flash chromatography ($CHCl_3$) to provide the acid (0.9 g, 5%) as a oil, HRMS (M+Li)$^+$ calcd for $C_7H_{13}O_2ClLi$ 171.0764, found 171.0766.

Example 11

With the aid of the general procedure for preparing compounds of the formula I and 1) the analogous procedures of Example 3, the compounds No. 1, 3, 6, 7 and 8 of Table 1 hereinafter are prepared, or 2) the analogous procedures of Example 9, the compound No. 4 of Table 1 hereinafter is prepared.

Example 11B

Preparation of 1-Thia-5,9,11-Triazacyclohexadecane, 7-Hydroxy-9-(3-Methylbutyl)-4,10-Dioxo-6-(Phenylmethyl)-, 1, 1-Dioxide, Cis-

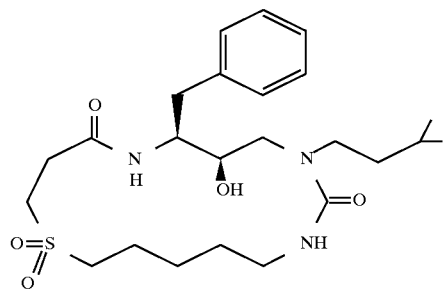

17

1-Thia-5,9-11-triazacyclohexadecane, 7-hydroxy-9-(3-methylbutyl)-4,10-dioxo-6-(phenylmethyl)-,1,1-dioxide,cis- To a solution of 5 (15 mg, 0.033 mmol) in anhydrous THF (4 mL) at 0°–5° C. was added 3-chloroperbenzoic acid (55%, 23 mg, 0.073 mmol). The mixture was stirred at 0°–5° C. for 15 minutes then at room temperature until complete by TLC (45 minutes), diluted with ethyl acetate, washed with 5% aqueous $NaHCO_3$, brine, dried ($MgSO_4$), filtered and evaporated. Purification by flash chromatography [hexane-ethyl acetate (30–100%] afforded 17 (11 mg, 69%) as an amorphous solid, $R_f$ 0.42 [$CH_2Cl_2$—MeOH (1%)], HRMS MH$^+$ calcd. for $C_{24}H_{40}N_3O_5S$ 482.2689, found 482.2717.

Example 11C

Preparation of 2-Oxa-4,8,10,14-Tetraazapentadecan-15-oic Acid, 6-Hydroxy-8-(3-Methylbutyl)-3,9-Dioxo-1-Phenyl-5-(Phenylmethyl)-, 1,1-Dimethylethyl Ester, (S)-

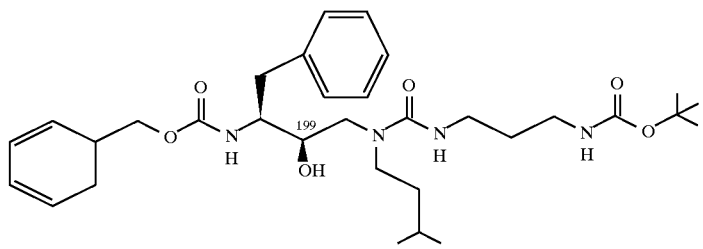

18

Curtius rearrangement of N-t-Boc-2-aminobutyric acid (Sigma, 300 mg, 1.48 mmol) as described for the preparation of 12 provided after purification by flash chromatography [CH$_2$Cl$_2$—MeOH (1–3%)] 18 (278 mg, 32%) as an oil, R$_f$ 0.42 [CH$_2$Cl$_2$—MeOH (5%)].

Example 11D

Preparation of Butanoic Acid, 4-[[3-[[[[3-[[(1,1,-Dimethylethoxy) Carbonyl]Amino]Propyl]Amino]Carbonyl] (3-Methylbutyl)Amino]-2-Hydroxy-1-(Phenylmethyl)Propyl] Amino]-4-Oxo-3-[ [Phenylmetboxy)Carbonyl]Amino]-,1,1-Dimethylethyl Ester, [R-(R*,S*,S*)]- and evaporated. Purification by flash chromatography [CH$_2$Cl$_2$—MeOH (1%)] provided 19 (144 mg, 65%) as an amorphous solid, R$_f$ 0.42 [CH$_2$Cl$_2$—MeOH (5%)], HRMS [M+Li]$^+$ calcd for C$_{40}$H$_{61}$N$_5$O$_9$Li 762.4629 found 762.4621.

Example 11E

Preparation of Carbamic Acid, [5-Hydroxy-3-(3-Methylbutyl)-2,8,11-Trioxo-5-(Phenylmethyl)-1,3,7,12-Tetraazacyclopentadec-9-YL]-, Phenylmethylester, (9S-Trans)-

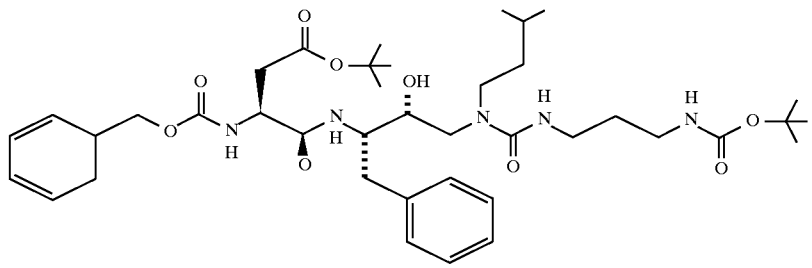

19

To a solution of 18 (168 mg, 0.29 mmol) in ethanol was added 5% palladium on carbon (40 mg). The mixture was hydrogenated at approx. 40 psi H$_2$ at room temperature until complete by TLC (4h). The catalyst was filtered and the solvent evaporated to provide the crude amine which was used without further purification. The amine was dissolved in anhydrous AMF (2.5 mL) under an atmosphere of nitrogen. To this solution was added 1-hydroxybenzotriazol (40 mg, 0.26 mmol), N-methylmorpholino, (26.3 mg. 0.26 mmol) and N-CBZ-β-t-butyl-L-aspartic acid N-hydroxysuccinimide ester (Sigma, 134 mg, 0.32 mmol). After stirring for 48 hours, the solution was diluted with ethyl acetate and washed with 0 0.25N HCl aqueous HCl, 5% aqueous NaHCO$_3$, and brine, dried (MgSO$_4$), filtered

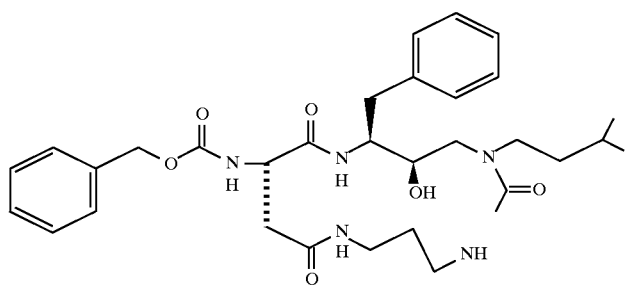

20

The protected intermediate 19 (53 mg, 0.07 mmol) was dissolved in cold (0°–5° C.) 70% azueous trifluoroacetic acid (3 mL) and stirred at 0°–5° C. for 1 hour then room temperature until complete by the (90 minutes). The solvent was removed by rotary evaporation and 4-toluenesulfonic acid (13 mg, 0.07 mmol) and toluene 10 mL were added.

Evaporation of the solvents in vacuo provided the crude toluenesulfonate which was used without further purification.

The toluenesulfonate was dissolved in anhydrous DMF (40 mL) and cooled to 0°–5° C. under an atmosphere of nitrogen. N-methylmorpholine (21 mg, 0.021 mmol) was added followed by the slow addition (approx. 1 hour) of diphenylphosphoryl azide [38.4 mg, 0.14 mmol, in anhydrous DMF (10 mL)]. The solution was stirred at 0° C. for 4 days then at room temperature for 2 days. Concentration to a viscous oil in vacuo, dilution with ethyl acetate and washing with 0.25N aqueous HCl, 5% aqueous $NaHCO_3$, brine, drying ($MgSO_4$) and evaporation provided the crude product purification by flash chromatography [$CH_2Cl_2$—MeOH (1–3%)] provided 20 as (15 mg, 37%) as an amorphous solid $R_f$ 0.32 [$CH_2Cl_2$—MeOH (5%)], HRMS $[M+Li]^+$ calcd. for $C_{31}H_{43}N_5O_6Li$ 588.3373, found 588.3352.

Example 12

Assays

Part A: Enzyme Assay

The compounds of the present invention are effective HIV protease inhibitors. Utilizing an enzyme assay as described below, the compounds set forth in Examples 4, 6, 10, 12 and shown in Table 1. The enzyme method is described below. The substrate is 2-aminobenzoyl-Ile-Nle-Phe(p-$NO_2$)-Gin-Arg$NH_2$. The positive control is MVT-101 [Miller, M. et al, Science, 246, 1149 (1989)]. The assay conditions are as follows:

Assay buffer: 20 mM sodium phosphate, pH 6.4
20% glycerol
1 mM EDTA
1 mM DTT
0.1% CHAPS The above described substrate is dissolved in DMSO, then diluted 10 fold in assay buffer. Final substrate concentration in the assay is 80 $\mu M$. HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10×the test concentration; 10 $\mu L$ of the enzyme preparation is added, the materials mixed and then the mixture is incubated at ambient temperature for 15 minutes. The enzyme reaction is initiated by the addition of 40 $\mu L$ of substrate. The increase in fluorescence is monitored at 4 time points (0, 8, 16 and 24 minutes) at ambient temperature. Each assay is carried out in duplicate wells.

TABLE 1

| No. | $R^1$ | $R^{2"}/R^{2'}$ | $R^4/R^5$ | n | ring size | X' | X | IC50 (nM) |
|---|---|---|---|---|---|---|---|---|
| 1 | Z—NH | H | H | 2 | 15 | S | NH | 340 |
| 2 | Z—NH | H | H | 3 | 16 | S | NH | 570 |
| 3 | Z—NH | H | H | 4 | 17 | S | NH | 1730 |
| 4 | Ac—NH | H | H | 3 | 16 | S | NH | 1600 |
| 5 | H | H | H | 3 | 16 | S | NH | 20%[a] |
| 6 | Z—NH | H | $CH_3$ | 3 | 16 | S | NH | 220 |
| 7 | Z—NH | $CH_3$ | H | 3 | 16 | S | NH | 1260 |
| 8 | Z—NH | H | $CH_3$ | 2 | 15 | S | NH | 140 |
| 9 | Qu—NH | H | H | 3 | 16 | S | NH | 510 |
| 10 | Z—NH | H | H | 3 | 16 | S | $CH_2$ | 47%[a] |
| 17 | H | H | H | 3 | 16 | $S(O)_2$ | NH | 21% |
| 20 | Z—NH | H | H | 1 | 1 | C(O)NH | NH | 16% |

[a]% at 10 microM
Qu is 2-quinolinylcarbonyl;
Z is bz-0-C(O) wherein bz is the benzyl.

12C ??? inhibited the HIV enzyme in an amount ranging from about 3 to about 100% inhibition at a concentration of 10 micromolar. The calculated $IC_{50}$ (inhibiting concentration 50%, i.e., the concentration at which the inhibitor compound reduces enzyme activity by 50%) values are The compounds of the present invention are effective antiviral compounds and, in particular, are effective retroviral inhibitors as shown above. Thus, the subject compounds are effective HIV protease inhibitors. It is contemplated that the subject compounds will also inhibit other viruses such as human T-cell leukemia virus, respiratory syncitial virus, hepadnavirus, cytomegalovirus and picornavirus by the proposed inhibition of post translational proteolytic processing events. Thus, the subject compounds are effective in the treatment and/or prophylaxis of retroviral infections.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, butyl chloride, bromides, and iodides; dialkyl sulfates like dimethyl, diethyl dibutyl, and diamyl sulfates, long chain halides such as decyl, lauryl, myristyl, and stearyl chlorides, bromides and iodides, aralkyl halides like benzyl and phenethyl bromides, and other. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular made of administration.

The dosage regimen to give relief from or ameliorate a disease condition (i.e., treatment) or protecting against the further spreading of the infection (i.e., prophylaxis) with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The parental as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pill, powders, and granules. In such solid dosage forms, the active compound may be admixed with at least one inert diluent such as sucrose, lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, olutions, suspensions, syrups, and elixirs containing inert diluents commonly used in the art, such as water.

Such compositions may also comprise adjuvants, such as wetting agents, emulsifying and suspending agents, and sweetening, flavoring, and perfuming agents.

Pharmaceutically acceptable carriers encompass all the foregoing and the like.

While the compounds of the invention can be administered as the sole active pharmaceutical agent, they can also be used in combination with one or more immunomodulators, antiviral agents or other antiinfective agents. For example, the compounds of the invention can be administered in combination with AZT or with N-butyl-1-deoxynojirimycin for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and condition.

What is claimed is:

1. A compound represented by the formula (I)

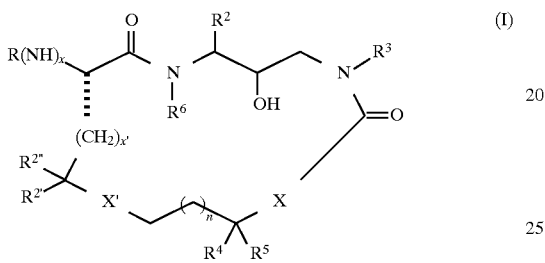

or a pharmaceutically acceptable salt, prodrug or ester thereof, wherein:

R represents hydrogen, alkoxycarbonyl, aryloxycarbonylalkyl, aralkoxy-carbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heteroaralkoxycarbonyl, heterocyclyalkanoyl, heterocyclylalkoxycarbonyl, heteroarylcarbonyl, heteroaryloxycarbonyl, heteroaroyl, alkyl, aryl, aralkyl, aryloxyalkyl, heteroaryloxylalkyl, hydroxyalkyl, alkylaminocarbonyl, arylaminocarbonyl, aralkylaminocarbonyl, aminoalkanoyl, aminocarbonyl, amincarbonyalkyl, alkylaminoalkylcarbonyl, and mono- and disubstituted aminoalkanoyl radicals wherein the substituents are selected from the group consisting of alkyl, aryl, aralkyl, cycloalkyl, cycloalkylalkyl, heteroaryl, heteroaralkyl, heterocycloalkyl, and heterocycloalkylalkyl radicals, or in the case of disubstituted aminoalkanoyl, said substituents along with the nitrogen atom to which they are attached form a heterocyclyl or heteroaryl radical;

x and x' independently represent an integer of 0 or 1;

$R^{2'}$ and $R^{2''}$ independently represent hydrogen, $R^2$ as defined hereinafter and $CO_2R$, $CH_2CO_2R$, $CH_2CONH_2$, $CH_2SO_2CH_3$, wherein R is independently as defined above;

$R^2$ represents alkyl, aryl, cycloalkyl, cycloalkylalkyl, and aralkyl radicals, which radicals are optionally substituted with a substituent selected from the group consisting of $-NO_2$, $-OR^{15}$, $SR^{15}$, and halogen radicals, wherein $R^{15}$ represents hydrogen and alkyl radicals;

$R^3$ represents alkyl, alkenyl, alkynyl, hydroxylalkyl, alkoxyalkyl, cycloalkyl, cycloalkylalkyl, heterocycloalkyl, heteroaryl, heterocycloalkylalkyl, aryl, aralky, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

n represents an integer of from 1 through 5;

$R^4$ and $R^5$ independently represent hydrogen and $R^2$ as defined above;

X represents O, S, $CH_2$ and $NR^1$ wherein $R^1$ is hydrogen and an alkyl radical;

X' represents $CH_2$, S, S(O). $S(O)_2$ and $R^{10}NH$ wherein $R^{10}$ represents $(CH_2)_qCO$ wherein q is an integer of 0 or 1;

$R^6$ represents hydrogen and alkyl radicals and wherein alkyl, alone or in combination, means a straight-chain or branched-chain alkyl radical containing from 1 to about 10 carbon atoms; alkenyl, alone or in combination, means a straight-chain or branched-chain hydrocarbon radical having one or more double bonds and containing from 2 to about 18 carbon atoms: alkynyl, alone or in combination, means a straight-chain hydrocarbon radical having one or more triple bonds and containing from 2 to about 10 carbon atoms; alkoxy, alone or in combination, means an alkyl ether radical wherein the term alkyl is as defined above; cycloalkyl, alone or in combination, means an alkyl radical which contains from about 3 to about 8 carbon atoms and is cyclic; aryl, alone or in combination means a phenyl or naphthyl radical which optionally carries one or more substituents selected from alkyl alkoxy halogen, hydroxy, amino and nitro; alkanoyl, alone or in combination, means an acyl radical derived from a 1 to 6 carbon atom alkanecarboxylic acid; heterocyclyl and heterocycloalkyl are saturated or partially unsaturated monocyclic, bicyclic or tricyclic heterocycles which contain one or more hetero atoms selected from nitrogen oxygen, and sulfur, which are optionally substituted on one or more carbon atoms by halogen, alkyl, alkoxy, or oxo or on a secondary nitrogen atom (—NH—) by alkyl, aralkoxycarbonyl, alkanoyl, phenyl or phenylalkyl or on a tertiary nitrogen atom (=N—) by oxido and heteroaryl is an aromatic monocyclic, bicyclic or tricyclic heterocycle which contains one or more hetero atoms selected from nitrogen, oxygen, and sulfur, which is optionally substituted on one or more carbon atoms by halogen, alkyl, alkoxy, or oxo or on a secondary nitrogen atom (—NH—) by alkyl, aralkoxycarbonyl, alkanoyl, phenyl or phenylalkyl or on a tertiary nitrogen atom (=N—) by oxido.

2. A compound of claim 1 wherein the stereo—chemistry about the hydroxy group is designated (R).

3. A compound of claim 1 wherein n is 1.

4. A compound of claim 1 wherein $R^2$ is phenylmethyl.

5. A compound of claim 1 wherein $R^3$ is isobutyl, isoamyl, n-butyl, benzyl, or cyclohexylmethyl.

6. A compound of claim 1 wherein $R^6$ is hydrogen.

7. A compound of claim 1 wherein X' is sulfur.

8. A compound of claim 1 wherein $R^4$ and $R^5$ are selected from hydrogen and methyl.

9. A compound of claim 1 wherein $R^{2'}$ and $R^{2''}$ are hydrogen or methyl.

10. A compound of claim 1 of the formula

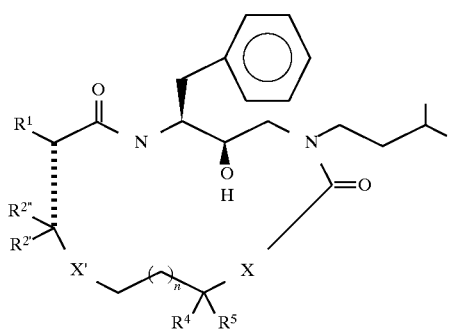

wherein $R^4$, $R^5$, $R^{2'}$ and $R^{2''}$ are as defined above and $R^1$ is $NH_2$, $CH_3C(O)NH$, quinolinyl-2-carbonylamino, or bzOC(O)NH wherein bz is benzyl; n is 2, 3 or 4; and X' is S, $S(O)_2$ or CONH.

11. A compound of claim 10 wherein $R^1$ is bzOC(O)NH; $R^{2''}$, $R^{2'}$, $R^4$ and $R^5$ are each hydrogen, n is 2; and X is NH.

12. A compound of claim 10 wherein R, $R^{2''}$, $R^{2'}$, $R^4$ and $R^5$ are each hydrogen, n is 3 and X is NH.

13. A compound of claim 10 wherein $R^1$ is bzOC(O)NH; $R^{2''}$ and $R^{2'}$, are each hydrogen; $R^4$ and $R^5$ are each methyl, n is 3 and X is NH.

14. A compound of claim 10 wherein $R^1$ is bzOC(O)NH; $R^{2''}$ and $R^{2'}$ are each hydrogen; $R^4$ and $R^5$ are each methyl; n is 2.

15. A compound of claim 10 wherein $R^1$ is bzOC(O)NH; $R^{2''}$, $R^{2'}$, $R^4$ and $R^5$ are each hydrogen; n is 3 and X is $CH_2$.

16. A pharmaceutical composition treating a disease advantageously affected by the inhibition of retroviral protease comprising an retroviral protease inhibitory amount of a compound of claim 1 together with a pharmaceutically acceptable carrier.

17. A method of treating a disease advangeously treated by the inhibition of retroviral protease in a human having the disease comprising a compound of claim 1 in a pharmaceutical dosage form.

18. A process for the preparation of a compound of claim 1 which comprises treating a compound of the formula

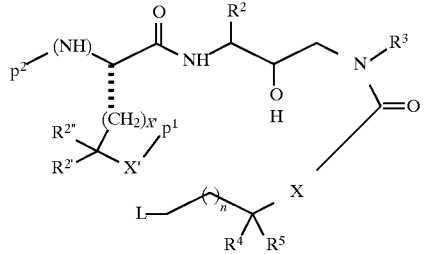

wherein $P^1$ and $P^2$ are each a protecting group and L is a leaving group; to remove the $P^1$ group to form a compound in which X' displaces L to form a compound of the formula (I)

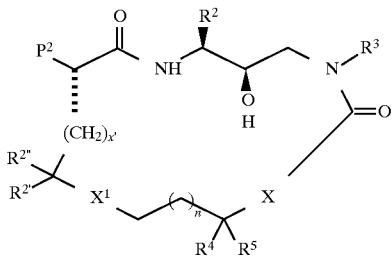

optionally removing $P^2$ and treating the resulting amine with RCl to replace the $P^2$ group with R.

* * * * *